United States Patent [19]

Chiu et al.

[11] Patent Number: 5,711,986

[45] Date of Patent: Jan. 27, 1998

[54] METHOD OF REPLACING FATS WITH SHORT CHAIN AMYLOSE

[75] Inventors: Chung-Wai Chiu, Westfield; William R. Mason, Somerville, both of N.J.

[73] Assignee: National Starch and Chemical Investment Holding Corporation, Wilmington, Del.

[21] Appl. No.: 394,929

[22] Filed: Feb. 24, 1995

Related U.S. Application Data

[63] Continuation-in-part of Ser. No. 42,935, Apr. 5, 1993, abandoned, and Ser. No. 79,961, Jun. 21, 1993, abandoned, which is a continuation of Ser. No. 615,570, Nov. 19, 1990, abandoned, which is a continuation-in-part of Ser. No. 258,231, Oct. 14, 1988, Pat. No. 4,971,723, said Ser. No. 42,935, is a continuation-in-part of Ser. No. 615,570, which is a continuation-in-part of Ser. No. 258,231.

[51] Int. Cl.$^6$ .................................................. A23G 3/00
[52] U.S. Cl. .................. 426/658; 426/549; 426/578; 426/661; 127/32; 127/65; 252/315.3; 435/98; 435/210
[58] Field of Search .......................... 426/549, 658, 426/578, 661; 252/315.3; 127/32, 33, 36, 38, 39, 40, 65, 67, 69, 70, 71; 435/98, 210

[56] References Cited

U.S. PATENT DOCUMENTS

| | | |
|---|---|---|
| 3,532,602 | 10/1970 | Seidman et al. . |
| 3,556,942 | 1/1971 | Hathaway . |
| 3,565,765 | 2/1971 | Heady et al. . |
| 3,632,475 | 1/1972 | Sugimoto et al. . |
| 3,666,557 | 5/1972 | Jensen et al. . |
| 3,729,380 | 4/1973 | Sugimoto et al. . |
| 3,730,840 | 5/1973 | Sugimoto et al. . |
| 3,766,011 | 10/1973 | Kurimoto et al. . |
| 3,879,212 | 4/1975 | Yoshida . |
| 3,881,991 | 5/1975 | Kurimoto et al. . |
| 3,922,196 | 11/1975 | Leach et al. . |
| 3,956,519 | 5/1976 | Evans et al. . |
| 3,962,465 | 6/1976 | Richter et al. . |
| 4,001,435 | 1/1977 | Hirao et al. . |
| 4,113,509 | 9/1978 | Leach et al. . |
| 4,211,842 | 7/1980 | Marshall . |
| 4,221,609 | 9/1980 | Hughes . |
| 4,510,166 | 4/1985 | Lenchin et al. . |
| 4,536,408 | 8/1985 | Morehouse et al. . |
| 4,560,651 | 12/1985 | Nielsen et al. . |
| 4,726,957 | 2/1988 | Lacourse et al. . |
| 4,886,678 | 12/1989 | Chiu et al. . |
| 4,911,946 | 3/1990 | Singer et al. . |
| 4,937,091 | 6/1990 | Zallie et al. . |
| 4,971,723 | 11/1990 | Chiu et al. . |
| 4,971,828 | 11/1990 | Abbas et al. . |
| 4,981,709 | 1/1991 | Furcsik et al. . |
| 4,985,082 | 1/1991 | Whistler . |
| 5,051,271 | 9/1991 | Iyengar et al. . |
| 5,089,171 | 2/1992 | Chiu ......................... 252/315.3 |
| 5,094,872 | 3/1992 | Furcsik et al. . |
| 5,110,612 | 5/1992 | Quarles et al. . |
| 5,194,284 | 3/1993 | Chiu et al. . |

FOREIGN PATENT DOCUMENTS

| | | |
|---|---|---|
| 0 327 288 | 8/1989 | European Pat. Off. . |
| 1559081 | 1/1969 | France . |
| 2661317 | 10/1991 | France . |
| 1423780 | 2/1976 | United Kingdom . |
| 2229077 | 9/1990 | United Kingdom . |
| 89/09793 | 10/1989 | WIPO . |
| 87/12403 | 12/1989 | WIPO . |
| WO 91/12728 | 9/1991 | WIPO . |

OTHER PUBLICATIONS

Anon., *Bulletin—Letterhead Food R.A.*, vol. 22, No. 6, (Jun. 1988).

Anon., "Fat Substitute Update," *Food Technology*, pp. 92–97, (Mar. 1990).

Braudo, Von E.E. et al., "Struktur and Eigenschaften von Maltodextrin Hydrogelen," *Starch/Stärke*, 31:188–194 (1979).

Harada, T., *Biotechnology and Genetic Engineering Reviews*, 1:39–63 (1984).

Manners et al., "The Fine Structure of Amylopectin," *Carbohydrate Research*, 90:99–110 (1981).

Norman, B.E., "Debranching Enzymes in Dextrose Syrup Production," *Recent Progress in Chemistry and Technology*, Academic Press, New York, (1982).

Rutenbeg, M.W., "Starch and Its Modifications," pp. 22–36, *Handbook of Water–soluble Gums and Resins*, Davidson, Editor, McGraw Hill, Inc., New York, (1980).

Slominska, L. et al., *Starch/Stärke*, 11:386–390 (1985).

Willox, J.C. et al., *MBAA Technical Quarterly*, 14:105–110 (1977).

*Primary Examiner*—Leslie Wong
*Attorney, Agent, or Firm*—Margaret B. Kelley

[57] ABSTRACT

A fat-like carbohydrate, containing 12 to 100%, by weight, short chain amylose, wherein the fat-like carbohydrate is used in foods in an amount effective to function as a replacement for up to 100%, by weight, of one or more fat(s) contained in foods. The short chain amylose may be prepared by the enzymatic debranching of starch, employing an enzyme which specifically degrades the alpha-1,6-D-glucosidic-linkages of the starch molecule. A method of replacing up to 100% of one or more fat(s) contained in foods, wherein the food containing the enzymatically debranched starch exhibits functional and organoleptic qualities equivalent to those of the food containing conventional amounts of fat. Also provided are foods containing the short chain amylose materials in place of fat, cream, oil, oil-in-water and water-in-oil emulsions and other lipids which are conventional components of the foods. These foods include: ice cream, spoonable and pourable salad dressings, margarine, low-fat spreads, low-fat cheeses, baked goods, breaded foods, sauces, whipped toppings, icings, puddings and custards, mayonnaise and coffee whiteners.

21 Claims, No Drawings

METHOD OF REPLACING FATS WITH SHORT CHAIN AMYLOSE

This application is a continuation-in-part (i) of Ser. No. 08/042,935, filed Apr. 5, 1993, now abandoned, which is a continuation-in-part of Ser. No. 07/615,570, filed Nov. 19, 1990, now abandoned, which is a continuation-in-part of Ser. No. 07/258,231 filed Oct. 14, 1988, now U.S. Pat. No. 4,971,723, and (ii) of Ser. No. 08/079,961, filed Jun. 21, 1993, now abandoned, which is a continuation of Ser. No. 07/615,570, filed Nov. 19, 1990, now abandoned, which is also a continuation-in-part of Ser. No. 07/258,231, filed Oct. 14, 1988, now U.S. Pat. No. 4,971,723.

This invention relates to a fat-like carbohydrate, comprising 12 to 100 percent short chain amylose, which is used as a functional replacement for fat in foods.

BACKGROUND OF THE INVENTION

Typical diets contain more fat than recommended by health experts in view of the epidemiological link between high dietary fat and increased health hazards. Typical diets also contain more calories than recommended by health experts for similar reasons. High fat content contributes directly to calorie-related health hazards because the caloric content of fats (9 Kcal/gram) is higher than that of other major nutrients, i.e., carbohydrates and proteins (4 Kcal/gram).

The replacement of fat in foods has proven a difficult challenge due to the unique flavor, mouthfeel, viscosity and other functional and organoleptic properties which characterize fat-containing foods. In addition, synthetic fat-replacers are subject to lengthy and expensive testing and review by regulatory agencies. Naturally-occurring fat-replacers, such as the protein- or carbohydrate-based products known in the art, are only useful in certain types of foods, or at certain temperatures, and otherwise are products of limited functionality which also may be subject to extensive regulatory testing and review. Anon. "Fat Substitute Update," *Food Technology* March, 1990, pp 92–97.

Among the carbohydrate-based fat-replacers are alpha-amylase converted tapioca and potato starches and maltodextrins having a dextrose equivalents (DE) of about 5 or less (e.g., U.S. Pat. No. 4,510,166 to Lenchin, et al., issued Apr. 9, 1985). Carbohydrates having a spheroidal shape and a particle-size distribution of about 0.1 to 2.0 microns are reported to have the organoleptic character of an oil-in-water emulsion in U.S. Pat. No. 4,911,946 to Singer, et al., issued Mar. 27, 1990. Gums and polydextrose have also been used as partial fat-replacers to provide bulk and viscosity to reduced-calorie or low-fat foods.

The short chain amylose employed as a fat-replacer herein has been used as a film-forming agent, (U.S. Pat. No. 3,881,991, to Kurimoto, et al., issued May 6, 1975; U.S. Pat. No. 3,879,212 to Yoshida, et al., issued Apr. 22, 1975; and U.S. Pat. No. 3,730,840 to Sugimoto, et al., issued May 1, 1973) and as an essential component of a partially debranched starch composition having unique gelling, lubricating and film-forming properties in aqueous dispersions (U.S. Pat. No. 4,971,723 issued Nov. 20, 1990 to Chiu). These debranched starch compositions are useful in imitation cheese as caseinate-replacers (U.S. Pat. No. 4,937,091 to Zallie, et al., issued Jun. 26, 1990) and in jelly gum confections as improved gelling agents (U.S. Pat. No. 4,886,678 to Chiu, et al., issued Dec. 12, 1989). The short chain amylose is preferably prepared by enzymatic debranching of starch.

Starch is a polysaccharide typically comprising a mixture of about 20–25% amylose and about 75–80% amylopectin which is organized into compact granular structures. Amylose is a linear polymer of D-anhydroglucose units which are linked by alpha-1,4-D-glucosidic bonds. Amylopectin is a large branched polymer of amylose chains linked by alpha-1,6-D-glucosidic bonds in a tree-like structure. Depending upon the variety of plant from which the starch is obtained, amylose ordinarily contains between 250 and 12,500 D-anhydroglucose units and amylopectin contains between 400,000 and 3,125,000 D-anhydroglucose units. As used herein, "short chain amylose" refers to linear polymers containing from about 15 to 65 anhydroglucose units linked by alpha-1,4-D-glucosidic bonds.

Enzymes, or mixtures of enzymes, which saccharify and debranch starch have been used in starch conversion processes for the commercial production of low molecular weight oligosaccharides and sugars, such as dextrose (glucose). Starch conversion is the degradation of starch to lower molecular weight components by treatment with acid, oxidizing agents, heat, alkali or alpha-amylase enzymes. Enzymatic conversion of starch typically involves preferential hydrolysis of the alpha-1,4-D-glucosidic bonds, and only limited, if any, hydrolysis of the alpha-1,6-D-glucosidic bonds (the branch points).

In the enzymatic conversion of starch to thin-boiling (low viscosity) starch; hydrolysis of branched fragments may be incomplete. For sugar production however, complete conversion of starch to sugar is desirable, and debranching enzymes have been used to degrade the branched alpha-limit dextrins (branched starch fragments which resist further hydrolysis by alpha-amylase) which remain intact after the enzymatic hydrolysis of alpha-1,4-D-glucosidic bonds. Glucoamylase, an enzyme which liquifies and saccharifies starch, has been employed for this purpose. Glucoamylase rapidly hydrolyzes alpha-1,4-D-glucosidic bonds and slowly hydrolyzes alpha-1,6-D-glucosidic bonds, releasing glucose. A debranching enzyme, such as pullulanase or isoamylase, which rapidly hydrolyzes only the alpha-1,6-D-glucosidic bonds, releasing short chain amylose, has been suggested for use in conjunction with glucoamylase and alpha-amylase to improve the efficiency of production of high dextrose syrups. These syrups are starting materials in the manufacture of crystalline dextrose and high fructose corn syrup. See Maize, *Recent Progress in Chemistry and Technology*, pp. 157–179, Academic Press, Inc. (1982); and Slominska, L., et al., *Starch/Starke*, 11:386–390 (1985).

Additionally, debranching enzymes (enzymes which release short chain amylose from starch) have been proposed for use in low calorie alcoholic beverage production to improve fermentability of branched starch fragments; in production of maltose from starch in conjunction with beta-amylase; in low DE maltodextrin (30–55 glucose units) production to induce proteins to aggregate in aqueous emulsions; and in enzymatic conversion of starch into a soluble syrup having a high quantity of disaccharides and trisaccharides. These debranching enzyme applications are directed to problems arising from the presence of branched starch or dextrin fragments following starch conversion processes. In each application, the debranching enzyme is employed in the complete conversion of starch to a variety of low molecular weight fragments such as sugars or maltodextrins. The thickening, adhesion and gelling characteristics of starch are lost.

The use of debranching enzymes to fully debranch starch, with hydrolysis of substantially all alpha-1,6-D-glucosidic bonds, so as to obtain pure, or amylopectin-free, low molecular weight amylose is taught in U.S. Pat. No. 3,730,840 to Sugimoto, et al., U.S. Pat. No. 3,881,991 to Kurimoto, et al., and U.S. Pat. No. 3,879,212 to Yoshida. These patents do not teach the conversion of starch to sugars and other soluble fragments. The object of these patents is to produce pure short chain amylose. The presence of any residual amylopectin is taught to be objectionable.

The background of enzyme-related starch technology does not suggest that carbohydrate compositions useful as fat-replacers in foods may be prepared by employing debranching enzymes to debranch the amylopectin component of starch, yielding short chain amylose, and, optionally, native amylose, amylopectin and partially debranched amylopectin, with or without substantial conversion of the starch. Furthermore, nothing in the literature suggests the utility of an enzymatic process for debranching starch as a replacement, in whole, or in part, for processes that are commercially used to produce various carbohydrate-based fat-replacers.

SUMMARY OF THE INVENTION

Thus, provided herein are fat-replacers in the form of carbohydrates Comprising 12 to 100%, by weight, short chain amylose, preferably enzymatically debranched starches, for use in foods. Aqueous dispersions of these debranched starches are characterized by a variety of fat-like textures ranging from oily to creamy to waxy, and these starches may be selected to provide aqueous dispersions which are high strength gels or thermoreversible gels. These fat-replacers offer significant advantages over other fat-replacers in food applications where the demand for "natural" products persists. A thermally reversible starch gel is one which melts upon heating and reforms upon cooling. Gels prepared from unmodified starches are not thermally reversible.

This invention provides a fat-like carbohydrate, comprising 12 to 100%, by weight, short chain amylose, wherein the fat-like carbohydrate is used in foods in an amount effective to function as a replacement for up to 100%, by weight, of one or more fat(s) contained in foods. Typically, a 20–30%, by weight, aqueous dispersion of the fat-like carbohydrate is used to replace fat in foods. In a preferred embodiment the short chain amylose is prepared by the enzymatic debranching of starch, employing an enzyme which specifically degrades the alpha-1,6-D-glucosidic-linkages of the starch molecule. The short chain amylose may be used in a refined form or as a mixture, further comprising long chain amylose, amylopectin, or a combination thereof and may be modified by derivatization, conversion, or crosslinking, before or after debranching the starch, except that a converted starch containing greater than 40% by weight of amylose may not be used as the starting base starch for the enzymatic debranching. The short chain amylose may be derived from a waxy maize starch, corn starch, high amylose corn starch, tapioca starch, potato starch, wheat starch, rice starch, waxy rice starch, and other starches.

This invention also provides a method of replacing up to 100% of one or more fat(s) contained in a food, comprising:
  a) providing an enzymatically debranched starch, comprising 12 to 100%, by weight, short chain amylose;
  b) formulating the food such that up to 100%, by weight, of the fat in the food is removed from the formulation; and
  c) substituting the enzymatically debranched starch for the fat in the food;
wherein the food containing the enzymatically debranched starch exhibits functional and organoleptic qualities equivalent to those of the food containing fat.

Also provided are foods containing short chain amylose in place of fat, cream, oil, oil-in-water and water-in-oil emulsions and other lipids which are components of the foods in their native states. These foods include: ice cream, spoonable and pourable salad dressing, margarine, low-fat spreads, low-fat cheeses, baked goods, breaded foods, sauces, whipped toppings, icings, puddings and custards, mayonnaise and coffee whiteners.

DESCRIPTION OF THE PREFERRED EMBODIMENTS

The starches which may be enzymatically treated to prepare short chain amylose may be derived from any source, including corn, potato, sweet potato, wheat, rice, sago, tapioca, waxy maize, sorghum, and the like. Also included are the conversion products derived from any of the above starches except high amylose starch, including fluidity or thin-boiling starches prepared by oxidation, alpha-amylase conversion, mild acid hydrolysis or heat dextrinization. Crosslinked and derivatized starches, such as ethers and esters, and other modified starches may also be employed.

The starch will preferably be a gelatinized starch (a precooked, cold-water-swelling starch) and also may be a fluidity starch, other than a high amylose fluidity starch, converted by mild acid degradation, heat dextrinization, or any one of several methods that are well known in the art. See, e.g., M. W. Rutenberg, "Starch and Its Modifications" P. 22–36, in *Handbook of Water-Soluble Gums and Resins*, R. L. Davidson, editor, McGraw Hill, Inc., New York, N.Y., 1980. If desired, the starch, other than a high amylose starch, may be converted by treatment with an alpha-amylase to produce a fluidity starch in the manner disclosed in U.S. Pat. No. 4,726,957 to Lacourse, et al. A combination of one or more of these conversion techniques may be used. The conversion is typically carried out before derivatization or crosslinking, but may be carried out before or after the enzymatic treatment. Where a high viscosity debranched starch is desired, it is not desirable to convert the starch.

Where a low viscosity starch is desirable, a starch, such as waxy maize, which has been converted to a Water Fluidity (WF) of up to about 60 is preferred. Water Fluidity is an empirical measure of viscosity on a scale of 0–90, wherein fluidity is the reciprocal of viscosity.

For other products, derivatization to any degree of substitution or level of conversion that results in the desired viscosity and functional characteristics may be employed prior to, or following, enzymatic debranching. For example, if the debranched starch is employed as an emulsifying agent in foods, an octenylsuccinate derivative (OSA starch) is preferred. The starch is treated with octenylsuccinic acid anhydride to form a starch ester derivative containing from 0.25 to 3.0%, by weight, of octenylsuccinate.

In a preferred embodiment, the next step after preparing the starch derivative is to heat an aqueous dispersion of the derivatized starch to gelatinize the derivatized starch. The gelatinization process disrupts, in whole or in part, the associative bonding of the starch molecule within the raw starch granule, thereby making the molecule more accessible to the enzyme and permitting the enzyme to more easily and uniformly debranch the starch molecules. After a slurry of the starch has been gelatinized, the solids, temperature and pH of the dispersion are adjusted to provide optimum enzyme activity.

The optimum parameters for enzyme activity will vary depending upon factors including enzyme concentration, substrate concentration, pH, temperature, the presence or absence of inhibitors and other factors. Depending on the type of enzyme, or its source, various parameters may require adjustment to achieve optimum debranching rate. In general, enzymatic debranching is carried out at the highest feasible solids content to facilitate subsequent drying of the starch while maintaining optimum debranching rates. For example, for the pullulanase used herein to produce a starch suitable for use as a fat replacer, a precooked starch dispersion ranging up to 28% solids is preferred.

The practitioner will recognize that a higher solids starch system (e.g., above 50% solids) may be employed if the starch is gelatinized by a process which produces adequate mixing to uniformly blend the enzyme and the starch at higher solids. The practitioner also will recognize that the temperature, treatment time and other parameters of the enzymatic debranching process must be adjusted to the higher solids content. Processes which employ higher solids starch dispersions are intended to fall within the scope of this invention and may be used to prepare the short chain amylose.

Although the preparation of short chain amylose herein employs pullulanase (E.C. 3.2.1.41; pullulan 6-glucanohydrolase) as the enzyme, other endo-alpha-1,6-glucanohydrolases, such as isoamylase (E.C. 3.2. 1.68), or any other endo-enzyme which exhibits selectivity in cleaving the 1,6-linkages of the starch molecule, leaving the 1,4-linkages substantially intact and releasing short chain amylose, may be used.

In a preferred embodiment, the enzyme used is a heat stable pullulanase obtained from a novel species of Bacillus. This pullulanase will catalyze the hydrolysis of the alpha-1,6 linkages in pullulan and amylopectin, provided that there are at least two glucose units in the side chain. Pullulanase is a linear polymer consisting essentially of D-glucopyranosyl triose units joined by alpha-1,6 linkages.

Optimum concentrations of enzyme and substrate are governed by the level of enzyme activity which will vary depending upon the enzyme source, the enzyme supplier and the concentration of the enzyme provided in commercially available batches. Although the process of this invention makes use of an enzyme in solution, processes utilizing an enzyme immobilized on a solid support are intended to fall within the scope of this invention.

The reaction may proceed in the presence of buffers to ensure that the pH will be at the optimum level throughout the degradation. Buffers such as acetates, citrates, or the salts of other weak acids are acceptable. Other agents may be used to optimize enzyme activity. The reaction may be carried out in a pH range from about 3.0 to 7.5, with the preferred range being between 4.5 and 5.5, and the optimum being 5.0 when the temperature is 60° C. and the enzyme is the Bacillus pullulanase.

The aqueous starch dispersion should be held during the enzymatic debranching at a temperature of about 25°–100° C., the preferred range being 55°–65° C. and the optimum being 60° C. at pH 5.0 for the Bacillus pullulanase. However, if shorter treatment times are desired, a temperature range from 60°–65° C. or a higher enzyme concentration may be used. Alternatively, a higher temperature may be employed if a thermally stable debranching enzyme which yields short chain amylose from starch is selected for use herein. As with other parameters of the enzyme reaction, the preferred and optimum temperature ranges will vary with changes in other parameters such as substrate concentration, pH and other factors affecting enzyme activity, and can be determined by the practitioner.

The enzymatic treatment is permitted to continue until the desired amount of short chain amylose is produced. The progress of the enzymatic treatment may be measured by various methods. If all critical parameters have been established for achieving a particular starch composition, then the treatment may be allowed to proceed to a predetermined relative end point in time. The end point may be determined by change in viscosity of the starch dispersion, by gel permeation chromatography, by reducing group content, iodine reaction or by any other method known in the art for measuring the degree of enzymatic debranching of the starch molecule.

In a preferred embodiment, the debranching end point is measured by determining the viscosity of a starch dispersion at 72° F. (22° C.) using the funnel viscosity method set forth in Example 1, below. The funnel viscosity method is a rapid, simple method for determining viscosity, in which the amount of time needed for a standard quantity of starch slurry to flow through a standard size funnel is recorded.

In a second preferred embodiment, the degree of starch debranching is measured by gel permeation chromatography. After separating the starch into its different molecular weight fractions, the percentage of short chain amylose is determined by calculating the percentage, by weight, of the low molecular weight fraction of the partially debranched starch. It will be understood by the practitioner that these percentages are approximately equal to the amount of short chain amylose which has been liberated from the amylopectin by the debranching enzyme. Experimental error in gel permeation chromatography (e.g., due to contamination by the enzyme, or by sugars or dextrins introduced with the starch, the enzyme solution, the buffer or other process components) may result in a percent low molecular weight fraction which may range up to 5% more or less than the percent short chain amylose of the starch sample.

The percentage of short chain amylose needed for a particular application depends on the type of starch utilized, the presence and nature of any substituent groups and the degree, if any, of conversion. A higher percentage of short chain amylose generally provides better fat-like properties in foods. The practitioner will be able to select a suitable starch and determine the necessary debranching for any particular end use with a minimum of experimentation.

While any amylopectin-containing starch may be employed, the effects of enzymatic debranching will be more dramatic as the amylopectin content of the starch increases. Thus, although all commercially available starches may be employed herein, waxy maize which contains about 100% amylopectin is preferred. In a preferred embodiment, waxy maize starch, or some other waxy starch (e.g., waxy rice or barley starch), is debranched, yielding sufficient short chain amylose to create a mixture comprising from 12 to 100% short chain amylose, and preferably, from 35 to 100% short chain amylose. In some embodiments, in excess of 89% short chain amylose is preferred. This degree of debranching of waxy starches is preferred for creating a fat-like, lubricating texture in an aqueous starch dispersion. Converted, debranched waxy starches (e.g., 50 WF acid-converted waxy maize or waxy rice) also are preferred for preparing a thermally reversible gel and providing fat-like qualities in an aqueous starch dispersion.

For preparing a fat-replacer characterized by a high strength starch gel, partially debranched corn starch, comprising 10 to 45% short chain amylose, and preferably 15 to 40% short chain amylose, is preferred.

After the desired degree of starch debranching has been reached, the enzyme may be deactivated. Pullulanase is rapidly deactivated at temperatures above about 70° C., therefore, the reaction may be conveniently terminated by increasing the temperature of the starch dispersion to at least 75° C. for about 15 minutes.

Technics other than the enzymatic debranching of starch may be applied to the production of short chain amylose suitable for use as a fat-replacer in foods. For example, native amylose may be isolated from native starches and degraded by known conversion methods to yield lower molecular weight fragments, comprising short chain amylose. The converted starch fragments must then be separated to yield short chain amylose. Native or degraded starch mixtures also may be separated by centrifugation, filtration or other processes into their different molecular fractions, thereby producing short chain amylose. Any method known in the art for fractionating carbohydrate components may be employed herein to produce short chain amylose from polysaccharides, except that the short chain amylose may not be obtained by conversion of a base starch having an amylose content greater than 40% by weight (i.e., a high amylose starch base). Enzymatic technics (e.g., using phosphorylase, E.C. 2.4.1.1) may be used to polymerize glucose or other sugars and thereby produce short chain amylose. See. B. Pfannemüller, Die Stärke, 20:351 (1968) and 31:288 (1979).

If use in foods requires purification of the starch or the short chain amylose, the reaction impurities and by-products may be removed by dialysis, filtration, ion exchange processes, centrifugation or any other method known in the art for isolating and recovering the starch.

If a dried starch is desired for food applications, the starch may be dehydrated by any method known in the art.

It is to be understood that the invention includes starch blends which contain 12 to 100% short chain amylose. Thus, this invention includes blends of debranched starch and other components, such as chemically modified starches and other polymers, and includes multi-step processes in which an enzyme is employed in one step to debranch starch. For example, this invention includes multi-step processes and starch blends wherein the starch is converted (with the proviso the starch base does not contain greater than 40%, by weight, amylose), derivatized, crosslinked or otherwise modified in addition to being subjected to enzymatic debranching, or being blended with short chain amylose.

The short chain amylose may be employed alone in any edible formulation as a fat-replacer. The nature of the edible formulation will direct the selection of an appropriate short chain amylose-containing carbohydrate material from those disclosed herein. In a preferred embodiment, the edible formulation contains short chain amylose in place of fat, cream, oil-in-water or water-in-oil emulsions, or other lipid components present in the formulation in its conventional form or in the food's native state. The edible formulation may be liquid or dry, may be heat processed or frozen or refrigerated, and may contain appropriate fat replacement adjuncts (e.g., gums to enhance viscosity). The short chain amylose is stable to the temperature, oxygen content, enzymatic activity and pH conditions normally observed in the manufacture and storage of foods, pharmaceuticals and other edible formulations.

In a preferred embodiment, the edible formulation is selected from ice cream, spoonable and pourable salad dressing, margarine, low-fat spreads, low-fat cheeses, baked goods, breaded foods, sauces, whipped toppings, icings, puddings and custards, mayonnaise and coffee whiteners.

The short chain amylose may be added to the edible formulation as a powder or as a liquid dispersion, preferably an aqueous dispersion, comprising 20 to 30 percent, by weight, short chain amylose. The dispersion may be used with or without cooking, depending upon the particular food application, and the cooking way be carried out before, during or after other steps needed to formulate the food.

The following examples will more fully illustrate the embodiments of this invention. In these examples, all parts and percentages are given by dry weight basis and all temperature are in degrees Celsius unless otherwise noted.

EXAMPLE 1

This example illustrates the preparation of representative partially debranched starches by the process of this invention.

The starches were converted, derivatized or crosslinked, where applicable, prior to gelatinization and treatment with pullulanase. To convert the starch, a slurry of 100 parts of starch in 150 parts of water was heated to 52° C., the indicated amount of hydrochloric acid (1.75%) was added, and the mixture was stirred for 16 hours at 52° C. The hydrolysis was stopped by neutralizing the mixture with alkali (a solution of 3% sodium hydroxide) to a pH of 5.5. The converted starch was recovered by filtration, washed and dried.

STARCH DERIVATIZATION

To prepare the octenylsuccinate derivative, 100 parts of starch was slurried in 150 parts water, the pH was adjusted to 7.5 with sodium hydroxide, and the indicated amount of octenylsuccinic anhydride was added slowly while the pH was maintained at 7.5 with alkali. The reaction was complete when no further addition of alkali was necessary. The pH was adjusted to between 4.0 and 6.5 and the resulting derivatives were recovered by filtration, washed and dried.

To prepare the acetate derivative, 100 parts of the starch was slurried in 150 parts by water, adjusting the pH to 8.3 with 3% sodium hydroxide solution, and slowly adding the indicated amount of acetic anhydride while maintaining the pH at 8.3 with the above alkali. The reaction was complete when no further addition of alkali was necessary. The pH was adjusted to between 4.0 and 6.5 and the resulting derivative was recovered as above.

The crosslinked starch was prepared by slurring 100 parts of starch in 150 parts water, adding 0.8 parts sodium hydroxide, 1.0 parts sodium chloride, and then adding the indicated amount of phosphorus oxychloride. The slurry was agitated for 3 hours at room temperature. When the reaction was completed, the pH was adjusted to 5.5 with acid. The starch was recovered by filtration, washed and dried.

STARCH DEBRANCHING

An aqueous slurry (20–30% solids) was prepared employing the desired starch. The aqueous starch slurry was jet-cooked at approximately 300° F. (149° C.) to gelatinize the starch. The cooked starch dispersion was placed in a constant temperature bath at 58°–60° C. with constant stirring. The pH was adjusted to 5 with 3% hydrochloric acid.

Depending on the type of starch used and its amylopectin content, between 0.5 and 10.0 mls of pullulanase per 100 g of starch were added to the cooked starch dispersion. The pullulanase (E.C. 3.2.1 41, pullulan 6-glucano-hydrolase) which was used is produced by a novel species of Bacillus. This enzyme (PROMOZYME®) was obtained from Novo Industri A/S of Denmark. The enzymatic activity of PROMOZYME in a 1.25 g/ml solution is standardized at 200

PUN/ml of solution. One PUN (Pullulanase Unit Novo) is the amount of enzyme which, under standard conditions, hydrolyzes pullulan, liberating reducing carbohydrate with a reducing power equivalent to 1 micro-mol glucose per minute. The procedure for determining PUN is available from Novo Industri A/S.

Thus, in the starch dispersion employing corn starch, 125 PUN of pullulanase per 100 g corn starch was added to the dispersion. For the waxy maize starch slurry (with higher amylopectin content), 750 PUN of pullulanase per 100 g waxy maize starch was added to the dispersion.

The amount of debranching was measured initially by the funnel viscosity test and subsequently by gel permeation chromatography.

FUNNEL VISCOSITY MEASUREMENT

To measure funnel viscosity at 19% solids, 38 g of the starch (anhydrous basis) was weighed into a tared 250 ml beaker (stainless steel) containing a thermometer and brought to 200 g total weight with distilled water. The sample was mixed to dissolve any lumps and heated or cooled to 72° F. (22° C.). A total of 100 ml of the cooked starch dispersion was measured into a graduated cylinder. It was then poured into a calibrated funnel while using a finger to close the orifice. A small amount was allowed to flow into the graduate to remove any trapped air, and the complete balance remaining in the graduate was poured back into the funnel. Using a timer, the time required for the 100 ml samples to flow through the apex of the funnel was recorded.

The funnel was a standard 58°, thick-wall, resistance glass funnel whose top diameter was about 9–10 cm with the inside diameter of the stem being about 0.381 cm. The funnel was calibrated so as to allow 100 ml of water to go through in 6 seconds using the above procedure.

CORN STARCH (CAUSTIC) FUNNEL VISCOSITY

Due to retrogradation of the starch which occurs when using corn starch, the funnel viscosity measurement was modified as follows for debranched corn starch:

1. the starch sample weight was reduced to 15 g (anhydrous basis);
2. sufficient hot (at least 90° C.) water was added to the starch to bring it to 150 g total weight;
3. 15 g of 25% w/v sodium hydroxide solution was added to the hot starch slurry; and
4. with stirring, the slurry was cooled to 72° F. (22° C.) and the measurement carried out as set forth above.

GEL PERMEATION CHROMATOGRAPHY

Starches were prepared for analysis by slurrying 5 mg of starch in 4 ml of dimethylsulfoxide ("DMSO") containing 0.03M sodium nitrate and heating the slurry to 80° C. for at least 30 minutes to dissolve the starch. Samples (200 μl) were injected into an ALC/GPC-150C Chromatograph (Waters Associates, Milford, Mass.) (equipped with a Nelson 3000 Series Chromatography Data System and two PL gel mixed 10 μm columns (obtained from Polymer Laboratory, Amherst, Mass.), employing DMSO containing 0.03M sodium nitrate as the mobile phase) and eluted at a rate of 1 ml/min. The columns were calibrated using dextran standards (with molecular weights of 2,000; 20,000; 80,000; 500,000; and 2,000,000 obtained from Pharmacia Fine Chemicals, Piscataway, N.J.). The percentage short chain amylose was calculated from the relative area of the peak obtained within the molecular weight range from 500 to 20,000.

PREPARATION OF DEBRANCHED OSA WAXY MAIZE STARCHES

Employing the process set forth above, an OSA starch derivative was prepared by reacting 4,000 g of waxy maize starch with 1% octenylsuccinic anhydride. The starch was then jet cooked at pH 5.0 yield a 23% starch dispersion. Pullulanase (80 mls) was added to the dispersion at 58° C. with agitation. After 24, hours, the funnel viscosity was 35 seconds at 19% solids and 72° F. (22° C.).

The debranching was continued by adding an additional 80 mls of pullulanase at 58° C. and agitating the dispersion for an additional 3 hours. The pullulanase was deactivated by heating the dispersion to about 80° C. The funnel viscosity was 12 seconds at 19% solids and 72° F. (22° C.). The starch dispersion was spray dried at an inlet temperature of 200°–210° C. and an outlet temperature of 80°–90° C. The spray-dried starch was screened through #40 mesh screen.

A second sample of OSA waxy maize starch (4,000 g) was prepared and debranched in the same manner as the first sample, except that 20 mls of pullulanase was employed in a single addition. Debranching continued for two hours at which time the funnel viscosity was 50 seconds at 10% solids and 72° F. (220° C.). This sample was spray-dried in the same manner as the first sample.

EXAMPLE 2

This example illustrates the preparation of partially debranched starch employing the enzyme isoamylase (glycogen 6-glucano-hydrolase; E.C. 3.2.1.68).

A cooked, 24% solids, aqueous dispersion of waxy maize starch (2,500 g) was treated with 5,000 units of a *Pseudomonas amyloderamosa* isoamylase (obtained from Sigma Chemical Company, St. Louis, Mo.). One unit of this isoamylase causes an increase in absorbance ($A_{610}$) of 0.1 in 1 hour using rice starch as a substrate.

The starch dispersion was heated to 45° C. at pH 4.0, the enzyme was added and the mixture was stirred for 26 hours. A portion of the mixture was removed, heated to 80° C. to deactivate the enzyme, and spray-dried and screened as in Example 1. The remaining portion of the starch mixture was enzymatically treated for a total of 43 hours, at which time the enzyme was deactivated and the starch dried and screened as above.

The quantity of short chain amylose obtained from isoamylase hydrolysis was measured with gel permeation chromatography. The 26 hour sample contained 21.9% and the 43 hour sample contained 28.4% short chain amylose.

EXAMPLE 3

This example illustrates the relationships between treatment time, funnel viscosity (or Water Fluidity) and percentage short chain amylose of the starches of this invention.

The partial enzymatic debranching process of Example 1 was carried out on the starches listed in Table I.

The funnel viscosity and percent short chain amylose were measured by the methods as set forth above. Results are shown in Table I.

The results show generally that as reaction time increases, the percent short chain amylose increases and the funnel viscosity decreases in a non-linear fashion. Thus, one or more of these measurements may be employed to measure the progress of the enzymatic debranching.

EXAMPLE 4

This example illustrates that the starch of this invention may be used to create lubricity and fat-like texture in an aqueous starch dispersion.

11

A waxy maize starch was partially debranched by the method of Example 1 to a funnel viscosity of 10–12 seconds at 72° F. (22° C.) and 10% solids (about 50% short chain amylose).

Fat-like or lubricating properties of the starch were evaluated by dispersing 25 g. anhydrous, of starch in 75 g of distilled water. The dispersion was heated on a steam bath for 20 minutes, poured into a petri dish, refrigerated for one hour and subjectively evaluated. The partially debranched starch gel was spread on the palm of the hand and observed to have a lubricating, creamy touch. The gel was glossy and opaque.

Additional starches and starch blends were tested by the same method for fat-like properties in aqueous dispersions. These starches and starch blends and the test results are set forth in Table II. All samples exhibited fat-like properties, including blends of debranched waxy maize with tapioca maltodextrin or converted waxy maize or converted tapioca. The short chain amylose content of the debranched waxy maize starch ranged from 15 to 75%, by weight.

EXAMPLE 5

This example illustrates the preparation of a fat free frozen dairy dessert using short chain amylose as a fat replacer.

Frozen dairy desserts were prepared according to the following fat-free formulation and procedure.

FROZEN DAIRY DESSERT
FORMULATION I

| Ingredients | Percent By Weight |
| --- | --- |
| Skim Milk | 69.11 |
| Non-fat Dry Milk | 6.40 |
| Sugar (Cane) | 15.22 |
| Fat Replacer | 1.44 |
| Corn Syrup (Liquid, 36DE) | 6.42 |
| Stabilizer* | 0.87 |
| | 99.46 |

*SHEREX 302, a blend of gums, obtained from Microlife Technics, Inc., Sarasota, Florida.

To prepare the frozen dairy dessert mix, the stabilizer was added to the skim milk and mixed with a laboratory mixer (a T Line Lab stirrer, obtained from Talboys Engineering, Emerson, N.J.) for 5 minutes. The non-fat dry milk and a blend of the fat replacer and the sugar were added separately with mixing for 5 minutes after each addition. The corn syrup was warmed to about 130° F. (54° C.) and added to the milk mixture. The mix was pasteurized by heating the mix in a covered container to 160° F. (71° C.) for 30 minutes over a steam bath.

The pasteurized mix was homogenized in a Maton-Gaulin homogenizer (Model No. 15M, obtained from Maton-Gaulin, Everett, Mass.) at a pressure of 2,500 psi.

The viscosity of the mix was measured using a #2 Zahn Cup (a CVP type Boekel Viscometer, 44 cc capacity, obtained from Boekel Viscometer, Philadelphia, Pa.). The viscosity of a 45 ml sample was measured initially (at 160° F. (71° C.)); after 30 minutes of pasteurization (at 160° F. (71° C.)); after homogenization; and after cooling (to 40° F. (71° C.)). After cooling the mix was frozen in a Taylor Mate Ice Cream Freezer (obtained from Taylor Freezer, Rockton, Ill.). An 8 fluid ounce volumetric sample of the mix was weighed before and after freezing and the percent overrun was calculated from these weights.

12

The fat replacers used in the frozen dairy dessert, and the corresponding mix viscosity and mix percentage overrun are set forth in Table III.

These results show that all of the debranched starches (containing from 12.2 to 89.2% short chain amylose) permitted formulation of frozen dairy dessert mixes having acceptable viscosities and percentages of overrun that compare favorably to those of commercially used fat-free mixes (i.e., mixes containing either converted, pregelatinized tapioca starch as a fat-replacer or maltodextrin as a filler). Thus, the short chain amylose materials disclosed herein may be used to replace 100% of the fat contained in frozen dairy desserts, without loss of the functional processing benefits normally achieved by using cream, or some other fat in the dessert formulation.

Several of the short chain amylose-containing dessert formulations were organoleptically evaluated by a taste panel in a triangle test. The taste panel was instructed to compare the texture, iciness and creaminess qualities of the experimental samples to the same qualities of the maltodextrin-containing sample. The panel results showed a significant difference existed between the maltodextrin sample and two of the three experimental samples: the fully debranched potato starch and the converted tapioca starch. The experimental sample containing 60% short chain amylose (prepared from waxy maize starch at 1.44% of the mix) was not considered significantly different from the maltodextrin sample. Thus, when used to replace 100% of the fat in a frozen dairy dessert, the debranched starch provided acceptable organoleptic qualities.

EXAMPLE 6

This example illustrates the preparation of a frozen dairy dessert using short chain amylose as a partial fat replacer.

Frozen dairy desserts were prepared according to the following formulation and procedure.

FROZEN DAIRY DESSERT
FORMULATION II

Percent by weight[b]

| Ingredients | Control (6% butterfat) | Experimental (4% butterfat) |
| --- | --- | --- |
| Whipping Cream | 15.00 | 10.00 |
| Skim Milk | 64.98 | 67.91 |
| Non-Fat Dry Milk | 6.54 | 6.04 |
| Sugar (cane) | 10.00 | 10.00 |
| Corn Syrup (Liquid, 36 D.E.) | 5.00 | 5.00 |
| Stabilizer[a] | 0.55 | 0.55 |
| Fat Replacer[c] | — | 0.50 |

[a]SHEREX 302, a blend of gums, obtained from Microlife Technics, Inc., Sarasota, Florida.
[b]All samples were prepared with the same percentage of milk solids, non-fat, and with 6% butterfat for the control; 4% butterfat for experimental samples, thereby providing one-third fat replacement in the experimental sample.
[c]See Table IV and description below.

The frozen dairy dessert mix was prepared by the method of Example 5, except that the whipping cream was added to the skim milk prior to the addition of other ingredients. The percentage overrun and Zahn cup viscosity measurements were made as in Example 5 for the samples listed in Table IV, below. Results are shown in Table IV.

TABLE IV

CHARACTERISTICS OF REDUCED-FAT FROZEN DAIRY DESSERTS

| Fat Replacer (seconds) After | | Zahn Cup Viscosity | | |
|---|---|---|---|---|
| Cooling 40° F. (4° C.) | Percentage Overrun | Initial 160° F. (71° C.) | 30 min. 160° F. (71° C.) | After Homogenization |
| Control 30.5 (6% butterfat) | 45.0 | 17.8 | 18.6 | 21.0 |
| Debranched 36.5 Waxy Maize Starch* (12.2% short chain amylose) | 38.4 | 17.3 | 17.7 | 22.5 |

*Prepared by the method of Example 1.

These results show that the short chain amylose permitted formulation of a reduced fat dessert mix suitable for use in a commercial processing system.

A taste panel evaluation of organoleptic qualities of the frozen dessert was conducted with the control and experimental sample of Table IV. A reduced fat sample containing a debranched waxy maize starch containing 31.7% of short chain amylose (prepared by the method of Example 1) also was compared to the control. The majority of the panelists preferred the experimental sample of Table IV over the control. The flavor, mouthful, creaminess and texture of the control and both experimental samples were acceptable. When rated on a scale of 1 (worst)–10 (best), 78% of the panelists gave the 12.2% short chain amylose sample a score of 8 or better for flavor and texture. In a preference test, the other reduced fat sample (31.7% short chain amylose) and the control were preferred equally by the taste panel.

EXAMPLE 7

This example illustrates the preparation of sugar cookies using short chain amylose as a fat replacer.

Sugar cookies were prepared according to the following formulation and procedure.

SUGAR COOKIES FORMULATION

| Ingredients Replacement | Control | One-Third Fat |
|---|---|---|
| Wheat flour | 40.27 | 40.27 |
| Baking soda | 0.69 | 0.69 |
| Butter | 30.31 | 20.16 |
| Whole dry egg | 1.66 | 1.66 |
| Sugar (confectioners) | 13.27 | 13.27 |
| Almond flavor | 0.19 | 0.19 |
| Vanilla flavor | 0.36 | 0.36 |
| Fat replacer* | — | 3.00 |
| Corn syrup (liquid, 42 DE) | 13.27 | 13.27 |
| Water | 5.00 | 9.00 |

*Debranched waxy maize starch containing 60% short chain amylose which was prepared by the method of Example 1.

The butter was whipped until smooth. Dry ingredients were blended and mixed into the butter with a Mixmaster mixer. Water and other liquid ingredients were added to the butter mixture and mixed until a uniform dough was obtained. Cookies were placed on a baking sheet and baked at 375° F. (191° C.) for 10 to 15 minutes.

Cookies were evaluated by a taste panel for appearance, texture and bite and the majority of the panelists found the reduced fat cookie acceptable.

EXAMPLE 8

This examples illustrates the preparation of pourable french salad dressing using short chain amylose as a fat replacer.

Pourable salad dressings were prepared according to the following formulation and procedure as shown in Table V.

All dry ingredients except the gums were blended together. The gums were slurried in a portion of the oil and mixed with the water in a Hobart Mixer (C100 Model, Whip attachment, obtained from Hobart, Troy, Ohio) at #1 speed for 3 minutes. The dry blend was added to the gum mixture, wetted at speed #2 and mixed for 3 minutes at #1 speed. The tomato paste, remaining oil, and vinegar were added in separate steps with mixing after each addition. The viscosity of the mixture was measured on a Brookfield Viscometer using a "C" bar at 10 rpms. The mixture was passed through a colloid mill (a ND1 Charlotte Colloid Mill, obtained from Chemicolloid Labs, Inc., Garden City Park. N.Y.) set at 30 holes.

The viscosity of sample A was 1500 cps; sample B was 1440 cps; and Control 1 was 4400 cps.

The dressings were evaluated for pourability, appearance and texture by a taste panel. Seven out of eight panelists found the reduced fat samples A and B acceptable. In a second taste panel test, eleven out of twelve panelists found the reduced fat Sample C acceptable in appearance, mouthfeel and creaminess.

Various modifications and improvements on the compositions herein will become readily apparent to those skilled in the art. Accordingly, the scope and spirit of the invention are to be limited only by the claims and not by the foregoing specification.

TABLE I

| Chain Amylose | Treatment | | Funnel Viscosity (seconds) | % Solids | % Short |
|---|---|---|---|---|---|
| | Starch | Time (hrs.) | | | |
| Waxy-Maize Acid-converted to 50 WF | | | | | |
| 1 | 0.5 | 110 | 19 | | 13.5 |
| 2 | 1.0 | 22 | 19 | | 26.3 |
| 3 | 20.0 | 20 | 19 | | 27.1 |
| 4 | 20.0 | 18 | 19 | | 31.8 |
| 5 | 25.0 | 14 | 19 | | 35.1 |
| 6 | 44.0 | 12 | 19 | | 48.0 |
| Waxy-Maize | | | | | |
| 1 | 0.25 | 110 | 19 | | 22.1 |
| 2 | 1.0 | 52 | 19 | | 23.8 |
| 3 | 20.0 | 20 | 19 | | 32.6 |
| 4 | 20.0 | 16 | 19 | | 40.0 |
| 5 | 24.0 | 12 | 19 | | 45.6 |
| 6 | 45.0 | 12 | 19 | | 51.9 |
| Corn* | | | | | |
| 1 | 1.0 | 97 | 10 | | 14.5 |
| 2 | 3.0 | 37 | 10 | | 21.9 |
| 3 | 5.0 | 30 | 10 | | 26.5 |

TABLE I-continued

| Chain Amylose | Treatment | | Funnel Viscosity (seconds) | % Solids | % Short |
|---|---|---|---|---|---|
| | Starch | Time (hrs.) | | | |
| 4 | 7.0 | 27 | 10 | | 24.9 |
| 5 | 24.0 | 18 | 10 | | 33.3 |
| 6 | 48.0 | 12 | 10 | | 47.5 |

*Caustic Funnel Viscosity.

TABLE II

CHARACTERISTICS OF AQUEOUS DISPERSIONS OF DEBRANCHED STARCHES

| Percent of Starch in Blend | | | | Converted Starch[e] | | |
|---|---|---|---|---|---|---|
| Debranched Starch Waxy Maize | | | Tapioca | 35 WF Waxy | 81 WF Waxy | Evaluation in Aqueous Dispersion |
| A[a] | B[b] | C[c] | Maltodextrin[d] | Maize | Maize | (25% solids dispersion) |
| 100 | — | — | — | — | — | glossy, opaque, creamy gel, spreadable |
| 80 | — | — | 20 | — | — | opaque, creamy, shortening |
| 60 | — | — | 40 | — | — | opaque, butter-like |
| 20 | — | — | 80 | — | — | opaque, oily |
| 50 | — | — | — | — | 50 | opaque, creamy, spreadable |
| 75 | — | — | — | — | 25 | opaque, creamy, spreadable |
| — | 100 | — | — | — | — | creamy, greasy, slight tack |
| — | 50 | — | — | — | 50 | creamy, buttery |
| — | — | 100 | — | — | — | creamy, spreadable gel |
| — | — | 50 | — | 50 | — | creamy, soft, greasy, spreadable gel |

[a]. 50% short chain amylose
[b]. 15% short chain amylose
[c]. >75% short chain amylose
[d]. an alpha-amylase converted pregelatinized tapioca starch, of the type disclosed in U.S. Pat. No. -A-4,510,166 to Lechin, et al.
[e]. acid-converted starches, converted by the method of Example 1.

TABLE III

CHARACTERISTICS OF FAT-FREE FROZEN DAIRY DESSERTS

| Fat Replacer Percent Short Chain Amylose[f] | Percentage Overrun | Zahn Cup Viscosity (seconds) | | | |
|---|---|---|---|---|---|
| | | Initial 160° F. (71° C.) | 30 Min After 160° F. (71° C.) | Homogenization | After Cooling 40° F. (4° C.) |
| Converted Tapioca Starch[a,b] | — | 21 | 26 | 27 | 61 |
| Debranched Waxy Maize Starch | | | | | |
| 60%[a] | — | 16 | 22 | 24 | 46.5 |
| 60% | — | 20 | 24 | 26 | 49 |
| 12.2% | 67.2 | — | — | — | 52.5 |
| 31.7% | 64.8 | 20 | 23 | 22.5 | 54.5 |
| 44.0% | 57.9 | — | — | — | 53 |
| 54.5% | 67.1 | 18 | 24 | 26 | 54 |
| 56.3% (Crystalline) | 73.4 | — | — | — | 56.4 |
| Debranched Potato Starch 89.2% | 80.5 | — | — | — | 52 |
| Debranched Modified Waxy Maize Starch[c] | 72.1 | 17 | 24 | — | 51.9 |
| Debranched Modified Waxy Maize Starch[d] | 80.1 | — | — | — | 51.7 |

TABLE III-continued

CHARACTERISTICS OF FAT-FREE FROZEN DAIRY DESSERTS

| Fat Replacer Percent Short Chain Amylose[f] | Percentage Overrun | Zahn Cup Viscosity (seconds) | | | |
|---|---|---|---|---|---|
| | | Initial 160° F. (71° C.) | 30 Min After 160° F. (71° C.) | Homogenization | After Cooling 40° F. (4° C.) |
| 74.7% Maltodextrin[e] | 76.7 | 18 | 23 | 23.2 | 48 |

[a]. Fat replacer was used at 1.75% of mix (for converted tapioca) and 1.23% of mix (for debranched waxy maize) rather than at 1.44% of mix as shown in Frozen Dairy Dessert Formulation I, above.
[b]. An alpha-amylase converted pregelatinized tapioca starch, of the type disclosed in U.S. Pat. No. -A-4,510,166 to Lechin, et al.
[c]. A stabilized, crosslinked waxy maize starch obtained from National Starch and Chemical Company.
[d]. A waxy maize starch derivative containing about 1% octenyl succinic anhydride (OSA) obtained from National Starch and Chemical Company.
[e]. MALTRIN 10, obtained from Grain Processing Corporation, Muscatine, Iowa.
[f]. All debranched starches were prepared by the methods of Example 1, and percent short chain amylose was determined by gel permeation chromatography.

TABLE V

POURABLE FRENCH SALAD DRESSING FORMULATION
Percentage by Weight

| Ingredients | Controls | | One-Third Fat Replacement | |
|---|---|---|---|---|
| C[d] | 1 | 2 | A[a] | B[a] |
| Vegetable oil | 38.2 | 38.2 | 25.60 | 25.60 | 25.6 |
| Water | 20.85 | 20.85 | 27.15 | 27.19 | 27.19 |
| Sugar | 11.70 | 11.70 | 11.70 | 11.70 | 11.70 |
| White Vinegar | 20.00 | 20.00 | 24.80 | 25.00 | 25.00 |
| Tomato Paste | 6.00 | 6.00 | 6.50 | 6.50 | 6.50 |
| Salt | 1.00 | 1.00 | 1.00 | 1.00 | 1.00 |
| Mustard Powder | 1.00 | 1.00 | 1.00 | 1.00 | 1.00 |
| Onion Powder | 0.5 | 0.5 | 0.5 | 0.5 | 0.5 |
| Monosodium Glutamate | 0.3 | 0.3 | 0.3 | 0.3 | 0.3 |
| KELTROL ®-T[c] | 0.1 | 0.1 | 0.1 | 0.1 | 0.1 |
| Propylene Glycol Alginate | — | 0.1 | 0.1 | 0.1 | 0.1 |
| Garlic Powder | 0.2 | 0.2 | 0.2 | 0.2 | 0.2 |
| Oleoresin paprika | 0.05 | 0.05 | 0.05 | 0.05 | 0.05 |
| Sodium benzoate | 0.05 | 0.05 | 0.05 | 0.05 | 0.05 |
| Potassium Sorbate | 0.05 | 0.05 | 0.05 | 0.05 | 0.05 |
| Fat Replacer[a] | — | — | 1.51 | 1.26 | 1.26 |
| Tween ®-60[b] | — | — | 0.2 | 0.2 | 0.2 |

[a]. Debranched waxy maize starch containing 60% short chain amylose which was prepared by the method of Example 1.
[b]. An emulsifier obtained from ICI Specialty Chemicals, Wilmington, Delaware.
[c]. Xanthan gum obtained from Kelco Division of Merck & Company, Inc., Chicago, Illinois.
[d]. Debranched waxy maize starch containing 78% short chain amylose (crystallized) which was prepared by the method of Example 1.

What is claimed:

1. A method of replacing one or more fat(s) in a liquid-containing food, which comprises the steps of (a) formulating the food in such a way that up to 100%, by weight, of the total fat(s) in the food are omitted and (b) substituting for the fat(s) an enzymatically debranched waxy starch consisting essentially of at least about 50% by weight short chain amylose and up to 50% by weight of debranched amylopectin, in powdered form or as a dispersion in the liquid, which debranched waxy starch, when dispersed in the liquid, is capable of imparting a lubricating, fat-like, creamy, spreadable texture to the liquid.

2. A food prepared by the method of claim 1.

3. The food of claim 2, wherein the food is selected from the group consisting essentially of ice cream, spoonable and pourable salad dressing, margarine, low-fat spreads, low fat cheeses, baked goods, breaded foods, sauces, whipped toppings, icings, puddings, custards, mayonnaise and coffee whiteners.

4. The method of claim 1, wherein the debranched starch is a debranched waxy maize, debranched waxy rice, or debranched waxy barley.

5. The method of claim 4, wherein the debranched starch is the debranched waxy maize which consists essentially of 50% short chain amylose.

6. The method of claim 4, wherein the debranched starch is the debranched waxy maize which consists essentially of 75% short chain amylose.

7. The method of claim 4, wherein the debranched starch is the debranched waxy maize which consists essentially of 100% short chain amylose.

8. The method of claim 1, wherein the waxy starch is modified by reaction with octenyl succinic anhydride.

9. The method of claim 8, wherein the debranched waxy starch is the debranched waxy maize and wherein the amount of octenyl succinic anhydride is 0.25–3% by weight based on the starch.

10. A method of replacing one or more fat(s) in a liquid-containing food, which comprises the steps of (a) formulating the food in such a way that up to 100%, by weight, of the total fat(s) in the food are omitted and (b) substituting for the fat(s) a mixture containing at least 50% by weight of an enzymatically debranched waxy starch consisting essentially of at least 50% by weight of short chain amylose and up to 50% by weight of debranched amylopectin and (ii) up to 50% by weight of a converted waxy starch, which mixture, when dispersed in the liquid, is capable of imparting a lubricating, fat-like, creamy, spreadable texture to the liquid.

11. The method of claim 10, wherein the debranched waxy starch is a debranched waxy maize, a debranched waxy rice, or a debranched waxy barley.

12. The method of claim 11, wherein the debranched starch is the debranched waxy maize and the debranched waxy maize consists essentially of 50%, 75%, or 100% short chain amylose.

13. The method of claim 10, wherein the converted waxy starch is an acid-converted starch.

14. The method of claim 13, wherein the acid-converted waxy starch is an acid-converted waxy maize.

15. The method of claim 14, wherein the acid-converted waxy maize has a water fluidity of up to 60.

16. The method of claim 10, wherein the debranched waxy starch is a debranched waxy maize and wherein the converted waxy starch is an acid-converted waxy maize.

17. The method of claim 16, wherein the acid-converted waxy maize has a water fluidity of up to 60.

18. The method of claim 10, wherein the debranched waxy starch is a waxy maize modified by reaction with octenyl succinic anhydride.

19. The method of claim 18, wherein the amount of the octenyl succinic anhydride is 0.25–3% by weight based on the starch.

20. A food prepared by the method of claim 10.

21. The food of claim 20, wherein the food is selected from the group consisting essentially of ice cream, spoonable and pourable salad dressing, margarine, low-fat spreads, low fat cheeses, baked goods, breaded foods, sauces, whipped toppings, icings, puddings, custards, mayonnaise, and coffee whiteners.

* * * * *